US007183096B2

(12) United States Patent
Bloom et al.

(10) Patent No.: US 7,183,096 B2
(45) Date of Patent: Feb. 27, 2007

(54) RAPID GROWING MICROORGANISMS FOR BIOTECHNOLOGY APPLICATIONS

(75) Inventors: Fredric R Bloom, Germantown, MD (US); Brian J Schmidt, Rockville, MD (US); Jhy-Jhu Lin, Potomac, MD (US)

(73) Assignee: Invitrogen Corporation, Carlsbad, CA (US)

( * ) Notice: Subject to any disclaimer, the term of this patent is extended or adjusted under 35 U.S.C. 154(b) by 302 days.

(21) Appl. No.: 10/704,912

(22) Filed: Nov. 12, 2003

(65) Prior Publication Data

US 2004/0053413 A1    Mar. 18, 2004

Related U.S. Application Data

(63) Continuation of application No. 09/599,452, filed on Jun. 22, 2000, now Pat. No. 6,709,852.

(60) Provisional application No. 60/139,889, filed on Jun. 22, 1999.

(51) Int. Cl.
*C12N 1/00* (2006.01)
*C12N 1/20* (2006.01)
*C12P 21/06* (2006.01)
*C12P 19/34* (2006.01)
*C12N 15/00* (2006.01)

(52) U.S. Cl. ..................... 435/243; 435/69.1; 435/91.1; 435/252.1; 435/252.33

(58) Field of Classification Search .................. None
See application file for complete search history.

(56) References Cited

U.S. PATENT DOCUMENTS

| 4,966,841 A | 10/1990 | Riley |
| 4,981,797 A | 1/1991 | Jessee et al. |
| 5,914,390 A | 6/1999 | Nathan et al. |
| 6,071,733 A | 6/2000 | Muramatsu et al. |
| 6,215,007 B1 | 4/2001 | Khosla et al. |

FOREIGN PATENT DOCUMENTS

| EP | 1 010 754 A1 | 6/2000 |
| WO | WO 99/11756 | 3/1999 |

OTHER PUBLICATIONS

Inui et al., Sequence Analysis of the Cryptic Plasmid pMG101 from *Rhodopseudomonas palustris* and Construction of Stable Cloning Vectors, Appl. and Envtl. Microbiol., 66:54-63, 2000.*
Jung et al, Isolation and Characterization of *Rhodopseudomonas palustris* P4 which utilized CO with the production of H2 Biotech. Letters, 21: 525-529, 1999.*
Peitzsch et al, *Alcaligenes eutrophus* as a Bacterial Chromate Sensor, Appl. and Envtl. Micro., 64: 453-458, 1998.*
Alerthum, et al., "Efficient ethanol production from glucose, lactose and xylose by recombinant *Escherichia coli*" Appl. Environ. Microbiol. 55:1943-1948, American Society for Microbiology (1989).

Bertani, G., and Weigle, J.J., "Host Controlled Variation in Bacterial Viruses," *J. Bacteriol*. 65:113-121, American Society for Microbiology (1953).
Bhandari, P., and Gowrishankar, J., "An *Escherichia coli* Host Strain Useful for Efficient Overproduction of Cloned Gene Products with NaCl as the Inducer," *J. Bacteriol*. 179:4403-4406, American Society for Microbiologyy (1997).
Bharathi, A., and Polasa, H., "Elimination of broad-host range plasmid vectors in *Escherichia coli* by curing agents," *FEMS Miicrobiol. Lett*. 87:37-40, Elsevier Science Publishers (1991).
Dower, W.J., et al., "High efficiency transformation of *E. coli* by high voltage electroporation," *Nucleic Acids Res*. 16: 6127-6145, Oxford University Press (1988).
Hall, B.G., "Adaptive mutations in *Escherichia coli* as a model for the multiple mutational origins of tumors," *Proc. Natl. Acad. Sci. USA* 92: 5669-5673, National Academy of Sciences (1995).
Hanahan, D., "Studies on Transformation of *Escherichia coli* with Plasmids," *J. Mol. Biol*. 166:557-580, Academic Press Inc. Ltd., London (1983).
Hanahan, D., et al., "Plasmid Transformation of *Escherichia coli* and Other Bacteria," *Methods Enzymol*. 204:63-113, Academic Press Inc. (1991).
Khosla, C., et al., "Targeted gene replacements in a *Streptomyces polyketide* synthase gene cluster: role for the acyl carrier protein," *Mol Microbiol*. 6: 3237-3249, Blackwell Publishing (1992).
Maloy, S.R., and Nunn, W.D., "Selection for Loss of Tetracycline Resistance by *Escherichia coli*," *J. Bacteriol*. 145:1110-1112, American Society for Microbiology (1981).
Mori, T., et al., "Circadian gating of cell division in cyanobacteria growing with average doubling times of less than 24 hours," *Proc. Natl. Acad. Sci. USA* 93: 10183-10188, National Academy of Sciences (1996).
Palazzolo, M.J., et al., "Phage lambda cDNA cloning vectors for subtractive hybridization, fusion-protein synthesis and Cre-*loxP* automatic plasmid subcloning," *Gene* 88:25-36, Elsevier Science Publishers B.V. (1990).
Porter, T.D., et al., "Expression of a functional 78,000 dalton mammalian flavoprotein, NADPH-cytochrome P-450 oxidoreductase, in *Escherichia coli*," *Arch Biochem Biophys*. 254:353-367, Academic Press (1987).
Rosas, S.B., et al., "Involvement of a Plasmid in *Escherichia coli* Envelope Alterations," *J. Bacteriol*. 155:402-406, American Society for Microbiology (1983).

(Continued)

*Primary Examiner*—David Guzo
*Assistant Examiner*—Michele K. Joike (57) ABSTRACT

The present invention provides novel rapidly growing microorganisms and methods for their use in cloning or subcloning nucleic acid molecules. The rapid growing microorganisms of the present invention form colonies more rapidly than microorganisms typically used in molecular biology and thus provide a significant improvement in in vitro cloning methods used extensively in molecular biology. The invention also relates to kits and compositions used in the methods of the invention.

16 Claims, 1 Drawing Sheet

OTHER PUBLICATIONS

Sykora, P., et al., "A Kinetic Model for Plasmid Curing," *Plasmid* 21:85-98, Academic Press, Inc. (1989).

Tolker-Nielsen, T., and Boe, L., "A Statistical Analysis of the Formation of Plasmid-Free Cells in Populations of *Escherichia coli*," *J. Bacteriol.* 176:4306-4310, American Society for Microbiology (1994).

Trevors, J.T., "Plasmid curing inn bacteria," *FEMS Microbiol. Reviews*, 32:149-157, Elsevier Science (1986).

Tucker, W.T., et al., "Structural and Functional Analysis of the *par* Region of the pSC101 Plasmid," *Cell* 38:191-201, MIT Press, Cambridge (1984).

Sambrook, J., et al., eds., "Bacterial Strain List: Table A.2," in *Molecular Cloning: A Laboratory Manual*, 2nd edition, Cold Spring Harbor Laboratory Press, Cold Spring Harbor, NY, pp. A.9-A.13 (1989).

* cited by examiner

FIGURE 1

RAPID GROWING MICROORGANISMS FOR BIOTECHNOLOGY APPLICATIONS

CROSS REFERENCE TO RELATED APPLICATION

The present application is a continuation of U.S. patent application Ser. No. 09/599,452, filed Jun. 22, 2000 now U.S. Pat. No. 6,709,852, which claims the benefit of U.S. Provisional Application No. 60/139,889, filed Jun. 22, 1999, the contents of which are entirely incorporated herein by reference.

BACKGROUND OF THE INVENTION

1. Field of the Invention

The present application relates to the field of biotechnology and, in particular, to the fields of cloning and protein expression.

2. Related Art

The fundamental process that sustains the ongoing biotechnology revolution is the cloning of DNA molecules for their further analysis or use. Cloning of DNA molecules has been practiced in the art for many years. A typical cloning protocol will involve identifying a desired DNA molecule, preparing a population of recombinant vectors by ligating the DNA molecule with a vector in a mixture of DNA molecule, vector and an appropriate ligase enzyme, transforming the population of recombinant vectors into a competent microorganism, growing the microorganism for some period of time sufficient to permit the formation of colonies, selecting colonies of microorganisms that potentially contain the desired DNA molecule correctly ligated in the vector, growing a sufficient quantity of each selected colony from which to isolate the recombinant vector, analyzing the isolated vector to ensure that the vector contains the desired DNA molecule and then growing a sufficient quantity of the microorganism that contains the correct recombinant vector to perform whatever subsequent manipulations are required. For details of various cloning procedures the reader may consult Sambrook, et al. 1989, Molecular Cloning: A Laboratory Manual $2^{nd}$ Ed. Cold Spring Harbor Laboratory Press, Cold Spring Harbor, N.Y., specifically incorporated herein by reference.

The typical cloning protocol outlined above thus includes at least three steps that involve growing of a microorganism. Since these growing steps generally require 12–16 hours and are usually performed as overnight incubations, the rate limiting steps for experiments involving cloning of a DNA fragment are the steps requiring growth of a microorganism. Although there are many variations on the basic practice of cloning, virtually all cloning methods require the insertion of the DNA molecule of interest into a microorganism and growth of the microorganism and, therefore, the speed of virtually every cloning methodology is limited by the rate of growth of the microorganism used for cloning.

For most cloning applications, the microorganism of choice is *Escherichia coli* (*E. coli*). Although numerous strains of *E. coli* are known, most cloning applications use one or another derivative of *E. coli* K-12. These derivatives suffer from the slow growth rate discussed above. Other known strains of *E. coli*, such as *E. coli* W (ATCC9637), have a rapid growth rate when compared to *E. coli* K-12; however, wild type strains of *E. coli* W and other rapid growing strains are not suitable for biotechnology applications for several reasons. First, the genetics of the organism have not been determined to the level of detail required by cloning applications. Thus, those skilled in the art would not know whether the genome of a microorganism contained the appropriate modifications of a number of genes that would make the microorganism suitable for biotechnology applications. For example, microorganisms are generally recA$^+$ which leads to the formation plasmid multimers and makes the microorganism less suitable for applications that involve the isolation of plasmid. Microorganisms typically contain numerous protease genes and may degrade overexpressed proteins thereby decreasing the yield of a desired protein product. Microorganisms typically contain a lac operon that does not permit alpha complementation and, therefore, the identification of recombinant vectors is more difficult. Further, many microorganisms contain endogenous plasmids that complicate the plasmid isolation steps necessary for cloning applications. Finally, microorganisms might contain genes coding for nucleases that could cause the degradation of exogenous plasmids.

For a large number of biotechnology applications, a crucial step in the development of the application involves cloning one or more fragments of DNA. Given the central role of cloning in the development of the biotechnology industry, there has long existed in the art a need for reagents that speed the process of cloning. In particular, there exists a need in the art for microorganisms that have a desirable genotype and a rapid growth rate and can be employed to speed the cloning process. The present invention meets this long felt need.

BRIEF SUMMARY OF THE INVENTION

The present invention provides microorganisms for biotechnology applications characterized by a rapid growth rate as compared to the microorganisms currently used for these applications. In particular, the present invention provides a rapid growing microorganism that preferably lacks endogenous plasmids and is, therefore, suitable for cloning applications. Because the microorganisms of the present invention form colonies faster than the microorganisms currently in use in cloning applications, the present invention provides an improvement in cloning desired nucleic acid molecules, allowing more rapid identification and isolation of recombinant vectors and clones of interest.

The present invention thus provides a method of cloning that employs a rapid growing microorganism. The method entails constructing a population of recombinant vectors, transforming competent microorganisms capable of rapid growth with the population of recombinant vectors, selecting a transformed microorganism containing one or more recombinant vectors of interest and/or isolating one or more recombinant vectors of interest from the transformed microorganism. In one embodiment, the rapid growing microorganism is of the genus *Escherichia*. In another embodiment, the rapid growing microorganism is an *E. coli*. In a further embodiment, the rapid growing microorganism is an *E. coli* strain W. In a preferred embodiment, the rapid growing microorganism is an *E. coli* strain W lacking endogenous plasmids. In other preferred embodiments, the rapid growing microorganism is selected from a group consisting of BRL3781, BRL3784 and recA$^-$ derivatives thereof. The cloning methods of the present invention may optionally include a step of growing transformed microorganism at an elevated temperature to increase the growth rate of the microorganism, for example, at a temperature greater than 37° C. In a preferred embodiment, the transformed microorganisms may be grown at about 42° C.

The present invention provides a method of producing a protein or peptide which comprises constructing a recombinant vector containing a gene encoding a protein or peptide of interest, transforming the vector into a competent microorganism capable of rapid growth and culturing the transformed microorganism under conditions that cause the transformed microorganism to produce said peptide or protein. In a preferred embodiment, the rapid growing microorganism is of the genus *Escherichia*. In another preferred embodiment, the rapid growing microorganism is an *E. coli*. In another preferred embodiment, the rapid growing microorganism is an *E. coli* strain W. Other embodiments include a microorganism deleted in the lon protease. In some preferred embodiments, the microorganism carries a gene encoding a T7 RNA polymerase (RNAP). In other preferred embodiments, the T7 RNAP gene is under the control of a salt inducible promoter. In another preferred embodiment, the rapid growing microorganism does not contain endogenous plasmids.

The present invention also includes a method of producing a microorganism for cloning comprising the steps of obtaining a rapid growing microorganism containing endogenous plasmids and curing the microorganism of endogenous plasmids. In a preferred embodiment, the rapid growing microorganism is of the genus *Escherichia*. In another preferred embodiment, the rapid growing microorganism is an *E. coli*. In another preferred embodiment, the rapid growing microorganism is an *E. coli* strain W. In a related aspect of the present invention, any desired modification or mutation may be made in the microorganisms of the present invention including, but not limited to, alteration of the genotype of the microorganism to a recA$^-$ genotype such as recA1/recA13 or recA deletions, a lacZ$^-$ genotype that allows alpha complementation such as lacX74 lacZΔM15 or other lacZ deletion, a protease deficient genotype such as Δlon and/or ompT$^-$, an endonuclease minus genotype such as endA1, a genotype suitable for M13 phage infection by including the F' episome, a restriction negative, modification positive genotype such as hsdR17($r_K^-$, $m_K^+$), a restriction negative, modification negative genotype such as hsdS20 ($r_B^-$, $m_B^-$), a methylase deficient genotype such as mcrA and/or mcrB and/or mrr, a genotype suitable for taking up large plasmids such as deoR, a genotype containing suppressor mutations such as supE and/or supF. Other suitable modifications are known to those skilled in the art and such modifications are considered to be within the scope of the present invention.

The present invention provides a method of transforming a competent microorganism capable of rapid growth including the steps of obtaining a recombinant vector and contacting a competent microorganism of the present invention with the recombinant vector under conditions which cause the rapid growing microorganism to be take up the recombinant vector. In a preferred embodiment, the rapid growing microorganism is of the genus *Escherichia*. In another preferred embodiment, the rapid growing microorganism is an *E. coli*. In another preferred embodiment, the rapid growing microorganism is an *E. coli* strain W. In another preferred embodiment, the rapid growing microorganism is an *E. coli* strain W lacking endogenous vectors. The methods of the present invention may optionally include the step of growing the transformed microorganism at elevated temperatures to increase the growth rate of the microorganism, for example, at a temperature greater than 37° C. In a preferred embodiment, the transformed microorganisms may be grown at about 42° C.

The present invention also includes kits comprising a carrier or receptacle being compartmentalized to receive and hold therein at least one container, wherein the container contains rapid growing microorganisms. The kit optionally further comprises vectors suitable for cloning. In a preferred embodiment, the kits may contain a vector suitable for recombinational cloning. In a preferred embodiment, the rapid growing microorganisms may be competent. In some preferred embodiments, the rapid growing microorganisms may be chemically competent. In other preferred embodiments, the rapid growing microorganisms may be electrocompetent. In some preferred embodiments, the kits of the present invention may include enzyme including, but not limited to, restriction enzymes, ligases, and/or polymerases. In other preferred embodiments, the kits of the present invention may include recombination proteins for recombinational cloning. The kits of the present invention may also comprise instructions or protocols for carrying out the methods of the present invention.

The present invention includes compositions comprising rapid growing microorganisms. In a preferred embodiment, the rapid growing microorganism may be a competent microorganism. In some preferred embodiments, the rapid growing microorganisms may be chemically competent. In other preferred embodiments, the rapid growing microorganisms may be electrocompetent. The compositions of the present invention may optionally comprise at least one component selected from buffers or buffering salts, one or more DNA fragments, one or more vectors, one or more recombinant vectors, one or more recombination proteins and one or more ligases. In a preferred embodiment, the compositions of the present invention may comprise a rapid growing microorganism in a glycerol solution. In other preferred embodiments, compositions of the present invention may comprise rapid growing microorganisms in a buffer. In preferred embodiments, the microorganisms of the present invention may be in a competence buffer. In other preferred embodiments, the compositions of the present invention may comprise a lyophilized rapid growing microorganism.

The present invention includes a method of making competent rapid growing microorganisms comprising the steps of obtaining a rapid growing microorganism, growing the rapid growing microorganism and treating the rapid growing microorganism to make it competent. In some embodiments of the present invention, treating the microorganisms may include the step of contacting the microorganisms with a solution containing calcium chloride. In other embodiments, treating may include the step of contacting the microorganisms with water. Embodiments of the invention may include the step of curing the rapid growing microorganism of endogenous plasmids. In a preferred embodiment, the rapid growing microorganism is of the genus *Escherichia*. In another preferred embodiment, the rapid growing microorganism is an *E. coli*. In another preferred embodiment, the rapid growing microorganism is an *E. coli* strain W.

DETAILED DESCRIPTION OF THE INVENTION

Definitions

In the description that follows, a number of terms used in recombinant DNA technology are utilized extensively. In order to provide a clear and more consistent understanding of the specification and claims, including the scope to be given such terms, the following definitions are provided.

Competent cells or competent microorganisms as used herein refers to cells or microorganisms having the ability to take up and establish exogenous DNA molecules. Competent cells include, but are not limited to, cells made competent by chemical means, i.e. chemically competent cells, as well as cells made competent for electroporation by suspension in a low ionic strength buffer, i.e. electrocompetent cells.

Expression vector as used herein refers to a vector which is capable of enhancing the expression of a gene or portion of a gene which has been cloned into it, after transformation or transfection into a host cell. The cloned gene is usually placed under the control (i.e., operably linked to) certain control sequences such as promoter sequences. Such promoters include but are not limited to phage lambda $P_L$ promoter, and the *E. coli* lac, trp and tac promoters, the T7 promoter and the baculovirus polyhedron promoter. Other suitable promoters will be known to the skilled artisan.

Gene as used herein refers to a sequence of nucleotides that is transcribed in a cell. The term includes sequences that code for proteins and/or peptides as well as other sequences that do not code for such proteins or peptides. Examples of genes that do not code for proteins include, but are not limited to, the genes for tRNA, rRNA and the like. A gene includes a promoter sequence to control the transcription of the gene. A gene may also contain other DNA sequence elements that regulate the amount or timing of transcription. Such sequences elements are seen to include, but are not limited to, enhancers and the like.

Cell or microorganism as used herein, and which terms may be used interchangeably with each other and with the terms "host cell" and "host cell strain," includes microorganisms that can be genetically engineered. Both gram negative and gram positive prokaryotic cells may be used in accordance with the present invention. Typical prokaryotic host cells that may be used in accordance with the present invention include, but are not limited to, microorganisms such as those of the genus *Escherichia* sp. (particularly *E. coli*), *Klebsiella* sp., *Streptomyces* sp., *Streptococcus* sp., *Shigella* sp., *Staphylococuss* sp., *Erwinia* sp., *Klebsiella* sp., *Bacillus* sp. (particularly *B. cereus, B. subtilis,* and *B. megaterium*), *Serratia* sp., *Pseudomonas* sp. (particularly *P. aeruginosa* and *P. syringae*) and *Salmonella* sp. (particularly *S. typhi* or *S. typhimurium*). It will be understood, of course, that there are many suitable strains and serotypes of each of the host cell species described herein, any and all of which may be used in accordance with the invention. Preferred as a host cell is *E. coli*, and particularly preferred are *E. coli* strains derived from *E. coli* W.

As used herein, a "derivative" of a specified microorganism is a progeny or other recipient microorganism that contains genetic material obtained directly or indirectly from the specified microorganism. Such a derivative microorganism may, for example, be formed by removing genetic material from a specified microorganism and subsequently introducing it into another microorganism (i.e., the progeny or other recipient microorganism) by any conventional methodology including, but not limited to, transformation, conjugation, electroporation, transduction and the like. A derivative may be formed by introducing one or more mutations into the genome of a microorganism. The mutations may be insertions into the genome of the microorganism. Alternatively, the mutations may be deletions of one or more bases from the genome of the microorganism. In some instances, the mutations may be the alteration of one or more bases in the genome of the microorganism. In addition, one microorganism is a derivative of a parent microorganism if it contains the genome of the parent microorganism but does not contain the same extrachromosomal nucleic acid molecules. Thus, a strain produced by curing endogenous vectors from a parent strain is a derivative of the parent strain. Examples of mutations or other genetic alterations which may be incorporated into the microorganisms of the present invention include, but are not limited to, mutations or alterations that create: a $recA^-$ genotype such as recA1/recA13 or recA deletions, a $lacZ^-$ genotype that allows alpha complementation such as lacX74 lacZΔM15 or other lacZ deletion, a protease deficient genotype such as Δlon and/or $ompT^-$, an endonuclease minus genotype such as endA1, a genotype suitable for M13 phage infection by including the F' episome, a restriction negative, modification positive genotype such as hsdR17($r_K^-$, $m_K^+$), a restriction negative, modification negative genotype such as hsdS20($r_B^-$, $m_B^-$), a methylase deficient genotype such as mcrA and/or mcrB and/or mrr, a genotype suitable for taking up large plasmids such as deoR, a genotype containing suppressor mutations such as supE and/or supF. Other suitable modifications are known to those skilled in the art and such modifications are considered to be within the scope of the present invention.

Insert or inserts as used herein refers to one or more desired nucleic acid segments.

Isolating as used herein means separating the desired material, component, or composition at least partially from other materials, contaminants, and the like which are not part of the material, component, or composition that has been isolated. For example, "isolating a recombinant vector" means treating a cell, tissue, organ or organism containing the recombinant vector in such a way as to remove at least some of the other nucleic acid molecules (e.g., large nucleic acid molecules) with which it may be associated in the cell, tissue, organ or organism. As one of ordinary skill will appreciate, however, a solution comprising an isolated recombinant vector may comprise one or more buffer salts and/or a solvents, e.g., water or an organic solvent such as acetone, ethanol, methanol, and the like, and yet the nucleic acid molecule may still be considered an "isolated" nucleic acid molecule with respect to its starting materials.

Plasmid as used herein refers to a stable extrachromosomal genetic element.

Promoter as used herein refers to a DNA sequence that controls the transcription from another DNA sequence. A promoter is generally described as the 5'-region of a gene and is customarily located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Rapid growing microorganism as used herein refers to a microorganism that grows more rapidly than *E. coli* K-12 derived strains typically used in molecular biology applications. Rapid growing microorganisms produce colonies of a defined size from individual cells faster than non-rapid growing microorganisms. In general, a rapid growing microorganism will have an increased growth rate, such as a growth rate that is greater by 5%, 10%, 25%, 50%, 75%, 100%, 150%, 200% than the growth rate of a reference microorganism. Greater increases in growth rate may be included depending upon the microorganisms compared. A preferred reference strain is a strain such as *E. coli* MM294 (ATCC33625). Other suitable reference strains include DH5α and DH1OB (Life Technologies, Rockville, Md.) and any other strain routinely used in cloning applications. The invention also contemplates any microorganism which has an increased growth rate, such as a growth rate that is greater by 5%, 10%, 25%, 50%, 75%, 100%, 150%, 200%, when compared to *E. coli* W more particularly the specified *E. coli* W strains described herein. In the examples set forth below, rapid growing microorganisms of the present invention were identified by a comparison of the time necessary to grow a colony of 1 mm diameter on antibiotic containing LB plates after transformation with a plasmid conferring resistance to the antibiotic.

Rapid growing microorganisms of the present invention may also be identified by a comparison of the doubling time of a putative rapid growing microorganism to the doubling time of a reference strain. The rapid growing microorganisms of the present invention have a faster doubling time than known strains. Those skilled in the art a capable of determining the doubling time of a microorganism using standard techniques.

In determining whether a microorganism is a rapid growing microorganism, the growth rate is preferably compared to a reference strain having the same or similar genotype. For example, a putative rapid growing microorganism that is recA$^-$ should be compared to a recA$^-$ reference strain. Those skilled in the art will appreciate that a recA$^-$ microorganism may have a slower growth rate than a comparable recA$^+$ microorganism.

Recombinant microorganism as used herein refers to any microorganism which contains a desired cloned gene in a recombinant vector, cloning vector or any DNA molecule. The term "recombinant microorganism" is also meant to include those host cells which have been genetically engineered to contain the desired gene on the host chromosome or genome.

Recombinant vector as used herein includes any vector containing a fragment of DNA that is not endogenous to the vector.

Vector as used herein refers to a nucleic acid molecule (preferably DNA) that provides a useful biological or biochemical property to an Insert. Examples include plasmids, phages, viruses, autonomously replicating sequences (ARS), centromeres, transposons, and other sequences which are able to replicate or be replicated in vitro or in a host cell, or to convey a desired nucleic acid segment to a desired location within a host cell. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), T:A cloning, and the like) can also be applied to clone a fragment into a cloning vector to be used according to the present invention. The cloning vector can further contain one or more selectable markers suitable for use in the identification of cells transformed with the cloning vector.

The present invention may be used with vectors suitable for recombinational cloning as disclosed in U.S. Pat. No. 5,888,732 which is specifically incorporated herein by reference. Vectors for this purpose may comprise one or more engineered recombination sites. Vectors suitable for recombinational cloning may be linear or circular. When linear, a vector may include DNA segments separated by at least one recombination site. When circular, a vector may include DNA segments separated by at least two recombination sites. In one embodiment, a vector may comprise a first DNA segment and a second DNA segment wherein the first or the second may comprise a selectable marker. In other embodiments, a vector may comprise a first DNA segment and a second DNA segment, the first or the second segment comprising a toxic gene. In other embodiments, a vector may comprise a first DNA segment and a second DNA segment, the first or the second DNA segment comprising an inactive fragment of at least one selectable marker, wherein the fragment of the selectable marker is capable of reconstituting a functional selectable marker when recombined across the first or second recombination site with another inactive fragment of a selectable marker.

In accordance with the invention, any vector may be used. In particular, vectors known in the art and those commercially available (and variants or derivatives thereof) may be used in accordance with the invention. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, Perkin Elmer, Pharmingen, Life Technologies, Inc., and Research Genetics. Such vectors may be used for cloning or subcloning nucleic acid molecules of interest and therefore recombinant vectors containing inserts, nucleic acid fragments or genes may also be used in accordance with the invention. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, recombinational cloning transcription vectors, vectors for receiving large inserts (yeast artificial chromosomes (YAC's), bacterial artificial chromosomes (BAC's) and P1 artificial chromosomes (PAC's)) and the like. Other vectors of interest include viral origin vectors (M13 vectors, bacterial phage λ vectors, baculovirus vectors, adenovirus vectors, and retrovirus vectors), high, low and adjustable copy number vectors, vectors which have compatible replicons for use in combination in a single host (e.g., pACYC184 and pBR322) and eukaryotic episomal replication vectors (e.g., pCDM8). The vectors contemplated by the invention include vectors containing inserted or additional nucleic acid fragments or sequences (e.g., recombinant vectors) as well as derivatives or variants of any of the vectors described herein.

Expression vectors useful in accordance with the present invention include chromosomal, episomal and virus derived vectors, e.g., vectors derived from bacterial plasmids or bacteriophages, and vectors derived from combinations thereof, such as cosmids and phagemids, and will preferably include at least one selectable marker (such as a tetracycline or ampicillin resistance genes) and one or more promoters such as the phage lambda P$_L$ promoter, and/or the *E. coli* lac, trp and tac promoters, the T7 promoter and the baculovirus polyhedron promoter. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from InVitrogen; pGEX, pTrxfus, pTrc99a, pET-5, pET-9, pKK223-3, pKK233-3, pDR540, pRIT5 available from Pharmacia; and pSPORT1, pSPORT2 and pSV.SPORT1, available from Life Technologies, Inc. Other suitable vectors will be readily apparent to the skilled artisan.

Other terms used in the fields of recombinant DNA technology and molecular and cell biology as used herein will be generally understood by one of ordinary skill in the applicable arts.

The present invention provides novel microorganisms for biotechnology applications characterized by a more rapid growth rate than those microorganisms currently in use in the art. Both gram negative and gram positive prokaryotic cells may be used. The microorganisms of the present invention may be of any genus of microorganism known to those skilled in the art. The preferred characteristics of the microorganism are a rapid growth rate and the capability to be transformed with and to maintain exogenously applied DNA, in particular, to be transformed with and to maintain recombinant vectors. In preferred embodiments, host cells that may be used in accordance with the present invention include, but are not limited to, microorganisms such as those of the genera *Escherichia* sp. (particularly *E. coli*), *Klebsiella* sp., *Streptomyces* sp., *Streptocococcus* sp., *Shigella* sp., *Staphylococuss* sp., *Erwinia* sp., *Klebsiella* sp., *Bacillus* sp. (particularly *B. cereus, B. subtilis*, and *B. megaterium*), *Serratia* sp., *Pseudomonas* sp. (particularly *P. aeruginosa* and *P. syringae*) and Salmonella sp. (particularly *S. typhi* or *S. typhimurium*). In a preferred embodiment, the microorganisms of the present invention are of the genus *Escherichia*. In other preferred embodiments, the microorganisms of the present invention may be of the species *E. coli*. In a preferred embodiment, the microorganisms of the present invention may be of the *E. coli* strain W. In another preferred embodiment, the present invention includes derivatives of *E. coli* W that do not contain endogenous vectors. In other preferred embodiments, the microorganisms of the present invention may be *E. coli* strains K, B or C.

The microorganisms of the present invention may be identified by comparison to known bacterial strains. In general, comparison may be made to one or another derivative of *Escherichia coli* K-12. A well known strain that can serve as a reference strain is *E. coli* MM294 (ATCC33625). Other suitable reference strains include *E. coli* strains specifically describe herein. Thus, the invention contemplates any microorganism which grow at the same rate ar at a faster rate when compared to the *E. coli* W strains of the present invention. Such comparison can be made by any means known to those skilled in the art, including time to colony formation and/or doubling time.

The microorganisms of the present invention preferably form colonies more rapidly than the strains to which they may be compared. In particular, the microorganisms of the present invention will more rapidly form antibiotic resistant colonies after transformation with a vector containing an antibiotic resistance gene than the microorganisms of the prior art. To identify the microorganisms of the present invention, a potential candidate microorganism and a reference strain are spread on suitable solid plates, preferably agar media plates known to those skilled in the art, in parallel. The selection and preparation of a suitable solid plate are within the capabilities of those skilled in the art. A suitable plate may prepared using the medium recommended by the American Type Culture Collection or other suitable media for cultivation of the candidate microorganism. Alternatively, a comparison of the doubling time in liquid media may be used.

The plates may optionally contain an antibiotic if, for example, a competent reference strain is to be compared to a competent, putative rapid growing microorganism. Both microorganisms can be transformed with a vector that confers an antibiotic resistance to transformants. After transformation, the two microorganisms can be spread onto antibiotic plates in parallel and incubated at an appropriate temperature. The time to the appearance of antibiotic resistant colonies of a specified diameter can be determined. The rapid growing microorganisms of the present invention will form antibiotic resistant colonies of a specified size more rapidly than the microorganisms presently used for cloning applications. The plates are incubated at the same temperature and the time to colonies of a specified size is determined. In the examples below, a colony size of 1 mm diameter was used; however, any size may be selected and used. A microorganism that attains the specified size at a faster rate than the reference organism is considered to be a rapid growing organism.

The present invention also comprises a method of cloning employing the rapid growing microorganisms of the present invention. A population of recombinant vectors containing a desired insert may be constructed using techniques known in the art. For example, DNA of interest may be digested with one or more restriction enzymes to generate a fragment. The fragment may be purified on an agarose gel. A vector is prepared by digestion with the appropriate restriction enzymes. The vector may be further treated with other enzymes such as alkaline phosphatase or the Klenow fragment of DNA polymerase, and may be gel purified. The DNA fragment is ligated into the vector using an appropriate ligase enzyme to generate a population of recombinant vectors.

Other methods to produce a population of recombinant vectors may be used. For example, a population of recombinant vectors may be produced by recombinational cloning. An insert donor molecule is prepared comprising a DNA of interest flanked by a first and a second recombination site, wherein the first and the second recombination site do not recombine with each other. The insert donor molecule is contacted with a vector donor molecule comprising a third and a fourth recombination site, wherein the third and the fourth recombination sites do not recombine with each other. The insert donor/vector donor mixture is further contacted with one or more site specific recombination proteins capable of catalyzing recombination between the first and the third recombination sites and/or the second and the fourth recombination sites thereby allowing recombination to occur and generating a population of recombinant vectors.

Once constructed, the population of recombinant vectors is introduced into competent, rapid growing microorganisms using any one of the many techniques for the introduction of vector into a microorganism known to those skilled in the art. The transformed microorganisms are grown and recombinant microorganisms, i.e. those containing a vector, are selected. In one embodiment, the genotype of the microorganism is suitable for screening by alpha complementation and the selection step may include the use of a blue/white screen on solid plates containing a chromogenic substrate for β-galactosidase, such as X-gal. The vectors are isolated from the recombinant microorganism and analyzed for the presence of the DNA of interest.

The present invention also comprises a method of producing a desired protein or peptide utilizing the rapid growing microorganisms of the present invention. The method comprises constructing a recombinant vector containing a gene encoding the desired protein, transforming the vector into a competent, rapid growing microorganism and culturing the transformed microorganism under conditions that cause the transformed microorganism to produce the desired protein. The recombinant vector may be constructed using the methodology described above. In one embodiment, the recombinant vector will include an inducible promoter to control transcription from the gene coding for the desired protein. In other preferred embodiments, the genome of the microorganism will contain a gene for the T7 RNA polymerase under the control of an inducible promoter. In other preferred embodiments, the promoter controlling the expression of the T7 RNA polymerase will be inducible by the addition of salt to the growth media. In preferred embodiments, the rapid growing microorganism is of the genus *Escherichia*. In other preferred embodiments, the rapid growing microorganism is an *E. coli*. In other preferred embodiments, the rapid growing microorganism is an *E. coli* strain W. In another preferred embodiment, the rapid growing microorganism does not contain endogenous plasmid. In other preferred embodiments, the genotype of the microorganism has been altered to inactivate one or more genes coding for a protease and/or a ribonuclease. In one such preferred embodiment, the rapid growing microorganism does not contain a functional lon protease and/or a functional ompT protease. In other preferred embodiments, the rapid growing microorganism of the present invention does not have a functional rnaE gene and/or a functional rnaI gene. In other preferred embodiments the microorganism does not contain functional lon protease and/or a functional ompT protease and does not contain a functional ribonuclease encoded by the rnaE gene and/or the rnaI gene.

The present invention also includes kits comprising a carrier or receptacle being compartmentalized to receive and hold therein at least one container, wherein the container contains rapid growing microorganisms. The kit optionally further comprises vectors suitable for cloning. In a preferred embodiment, the kits may contain a vector suitable for recombinational cloning. Optionally, the kits of the present invention may contain enzymes useful for cloning. In a preferred embodiment, the kits may contain one or more recombination proteins. In a preferred embodiment, the rapid growing microorganisms may be competent. In some preferred embodiments, the rapid growing microorganisms may be chemically competent. In other preferred embodiments, the rapid growing microorganisms may be electrocompetent.

The present invention includes compositions comprising rapid growing microorganisms. In a preferred embodiment, the rapid growing microorganism may be a competent microorganism. In some preferred embodiments, the rapid growing microorganisms may be chemically competent. In other preferred embodiments, the rapid growing microorganisms may be electrocompetent. The compositions of the present invention may optionally comprise at least one component selected from buffers or buffering salts, one or more DNA fragments, one or more vectors, one or more recombinant vectors, one or more recombination proteins and one or more ligases. In a preferred embodiment, the compositions of the present invention may comprise a rapid growing microorganism in a glycerol solution. In other preferred embodiments, compositions of the present invention may comprise rapid growing microorganisms in a buffer. In preferred embodiments, the microorganisms of the present invention may be in a competence buffer. In other preferred embodiments, the compositions of the present invention may comprise a lyophilized rapid growing microorganism.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Strain Construction

All strains (listed in table 1) were constructed via bacteriophage P1 mediated transduction (Jeffrey Miller, Experiments in Molecular Genetics, Cold Spring Harbor Laboratories, 1972, specifically incorporated herein by reference). *E. coli* strains containing Tn10 insertions suitable for use with the P1 transduction technique can be obtained from the University of Wisconsin. The parental strain for this work was an *E. coli* W strain designated ATCC9637 obtained from the American Type Culture Collection (Manassas, Va.). The isolate received was resistant to bacteriophage P1. ATCC9637 was, therefore, converted to a P1 sensitive phenotype by infection with bacteriophage P1Cmts. P1Cmts is a bacteriophage P1 derivative which contains a temperature sensitive repressor and contains the chloramphenicol resistance gene. The bacteriophage forms P1 lysogens at 30° C. but replicates lytically at higher temperatures (>37° C.). *E. coli* W ATCC9637 was mixed with bacteriophage P1Cmts and chloramphenicol resistant colonies (which are P1Cm lysogens) were selected on LB chloramphenicol plates at 30° C. The chloramphenicol resistant strain was cured of the P1 lysogen by selection for surviving colonies at 42° C. The surviving colonies are now chloramphenicol sensitive. The P1 sensitive derivative of ATCC9637 (BRL3234) was then used for all subsequent work.

EXAMPLE 2

Construction of *E. coli* W endA$^-$

Competent cells of BRL3234 were prepared by a modification of the method of Hanahan (Doug Hanahan, J. Mol. Biol. 166,557, 1983) as described in U.S. Pat. No. 4,981,797 which is specifically incorporated herein by reference. The competent cells were transformed with pCM301 plasmid DNA (Tucker, et al., 1984, Cell 38(1):191–201.), a plasmid which is temperature sensitive for replication. Transformants were selected on ampicillin plates at 30° C. The introduction of the pCM301 plasmid into BRL3234 aided in the identification of endA$^-$ derivatives as described below.

Bacteriophage P1vir was grown on an *E. coli* strain, DB2, which contains an endA$^-$ mutation linked to the nupG::Tn10 transposon. The P1 lysate grown on DB3.2 was used to infect BRL3234/pCM301 with selection for tetracycline resistance. The tet$^r$ colonies were then screened for the linked endA$^-$ mutation by determining the ability of the transductants to degrade the pCM301 DNA after preparation of miniprep DNA. Those transductants which degraded the plasmid DNA were endA$^+$ and those which did not degrade pCM301 plasmid DNA were endA$^-$. The tetracycline resistant, endA$^-$ derivative of BRL3234/pCM301 was designated BRL3573. A derivative of BRL3573 lacking pCM301 was selected by streaking BRL3573 on an LB plate at 42° C. and screening colonies for ampicillin sensitivity.

The ampicillin sensitive derivative of BRL3573 was designated BRL3574. The nupG::Tn10 transposon was cured from BRL3574 using LB plates containing fusaric acid (Stanley Maloy and William Nunn, J. Bacteriol. 145: 1110, 1981). One tetracycline sensitive derivative of BRL3574 was designated BRL3580. BRL3580 is *E. coli* W endA⁻.

EXAMPLE 3

Construction of BRL3582 a RecA⁻ *E. coli* W.

A P1 Cm lysate was grown on BRL3229. BRL3229 contains a Tn10 transposon linked to a deletion mutation in recA. The P1 lysate was used to transduce BRL3580 and tetracycline resistant transductants were selected at 30° C. on LB plates containing 20 μg/mL tetracycline. The transductants were re-purified once on LB tetracycline plates and were then screened for sensitivity or resistance to nitrofurantoin on LB plates containing 4 μg/mL nitrofurantoin. RecA⁺ strains are resistant to nitrofurantoin whereas recA⁻ strains are sensitive to nitrofurantoin (S Jenkins and P. Bennett J., Bacteriol. 125:1214, 1976). One tetracycline resistant, nitrofurantoin sensitive derivative of BRL3580 was designated BRL3582.

EXAMPLE 4

Isolation of *E. coli* W Derivatives Lacking Native Plasmids

ATCC9637 and all strains derived from ATCC9637 up to and including BRL3580 contain 2 plasmids. The smaller plasmid is approximately 5.5 kb and the larger plasmid is >50 kb. The 5.5 kb plasmid was prepared from ATCC9637 by Lofstrand Labs (Gaithersburg, Md.). A restriction map of this plasmid is provided in FIG. 1.

Figure 1:
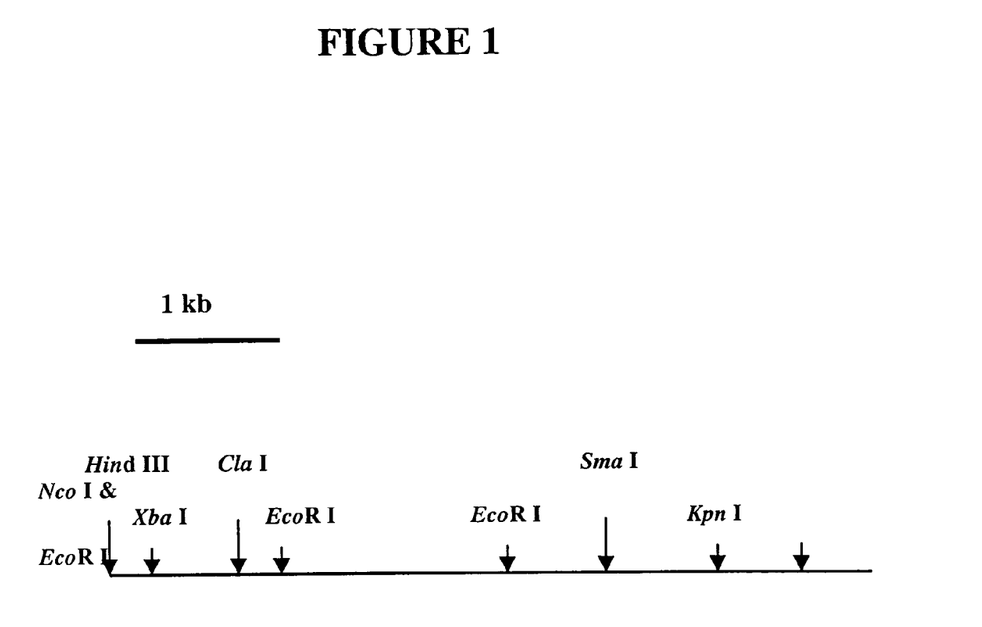
FIG. 1 is a restriction map of the 5.5 kb plasmid of ATCC9637.

The restriction map provided cloning sites which could be used to introduce a gene conferring resistance to ampicillin. The ampicillin resistance gene was isolated from plasmid pTrcN2, a pProEX-1 derivative (Life Technologies, Rockville Md.). The source of the ampicillin resistance gene is not critical. The following protocol will work with pProEX-1 and may be modified by those skilled in the art depending on the plasmid used as a source of the ampicillin resistance gene. 1 μg of plasmid pTrcN2 was digested with BspH1 (New England Biolabs) and the ends filled in with Klenow (Life Technologies, Inc). The 1008 bp DNA fragment containing the ampicillin resistance gene was purified by agarose gel electrophoresis. The 5.5 kb plasmid was digested with SmaI (New England Biolabs) and then treated with TsAP, a temperature sensitive alkaline phosphatase (Life Technologies, Inc.). The DNAs were mixed, treated with T₄ DNA ligase (Life Technologies, Inc) and transformed into competent ME DH10B cells (Life Technologies, Inc). Ampicillin resistant colonies were selected on LB plates containing 100 μg/mL ampicillin. Several ampicillin resistant colonies were grown in overnight culture and plasmid DNA was prepared and analyzed by electrophoresis on an agarose gel. All ampicillin resistant clones were found to have a plasmid with a molecular weight of 6.5 kb. The DH10B cells containing the plasmid (designated Wamp) were designated BRL3709.

The Wamp plasmid was transformed into competent cells of BRL3580 (*E. coli* W endA⁻) with selection for ampicillin resistance. BRL3580, as well as 5 ampicillin resistant transformants, were grown at 37° C. in LB broth containing 100 μg/mL ampicillin and the plasmid DNA was isolated and analyzed by agarose gel electrophoresis. The plasmid DNA from BRL3580 had a molecular weight of 5.5 kb whereas the ampicillin resistant transformants had plasmid DNA with a molecular weight of 6.5 kb indicating that the ampicillin resistance gene ~1 kb had been introduced into the 5.5 kb plasmid to give a 6.5 kb plasmid. Further, the 6.5 kb plasmid containing the ampicillin resistance gene had displaced the 5.5 kb plasmid. This is the expected result since both plasmids contained the same origin of replication. The *E. coli* W derivatives containing the 6.5 kb Wamp plasmid were designated BRL3711. Both BRL3580 and BRL3711 also contained the higher molecular weight (>50 kb) plasmid.

EXAMPLE 5

Curing BRL3711 of the 6.5 kb Wamp Plasmid

BRL3711 was cured of the Wamp plasmid by growth in LB broth containing SDS. SDS is well known in the literature as a compound which is used to cure plasmids from *E. coli* strains (A. Bharathi and H. Polasa, FEMS Microbiol. Lett, 84:37, 1991, Susana Rosos, Aldo Calzolari, Jose La Torre, Nora Ghittoni, and Cesar Vasquez, J. Bacteriol 155:402, 1983). BRL3711 was grown in LB broth containing 10% SDS at 30° C. After the culture reached the stationary phase, the culture was diluted 1:1000 into fresh LB+10% SDS for a second cycle. After the second cycle, the survivors were plated on LB plates 30° C. and colonies were screened for sensitivity to ampicillin. One isolate, designated BRL3718, was found to be sensitive to ampicillin indicating that the 6.5 kb plasmid had been cured. Miniprep DNA derived from BRL3711 as well as BRL3718 confirmed that BRL3711 had both the smaller and larger plasmids but that BRL3718 had only the larger plasmid.

EXAMPLE 6

Preparation of a Derivative of the Large Plasmid Containing an Antibiotic Resistance Gene.

To isolate *E. coli* W derivatives lacking the larger plasmid, antibiotic resistance genes were introduced into the larger plasmid using the Genome Primer System from New England BioLabs. The larger plasmid was isolated from BRL3718 using the standard alkaline-SDS lysis procedure (J. Sambrook, E. F. Fritsch, and T. Maniatis. 1989 Molecular Cloning: A Laboratory Manual $2^{nd}$ Ed. Cold Spring Harbor Laboratory Press. Cold Spring Harbor N.Y.). The Genome Priming System was used according to instructions provided by the manufacturer.

Approximately 80 ng of target plasmid DNA was mixed with 20 ng of donor plasmid DNA in a 20 μL reaction. One donor plasmid, pGSP1, donates the gene conferring resistance to kanamycin (Km). The second donor plasmid, pGSP2, donates the gene conferring resistance to chloramphenicol (Cm). The final reactions were diluted 1:10 in water and electroporated into EMax DH10B cells (Life Technologies, Inc.). 20 μL of cells were mixed with 1 μL of the diluted reaction and the cell-DNA combination was electroporated at 420 V, 4000 ohms, 2.4 kV, 16000 kV/cm. 10 μL were expressed in 1 mL SOC for 1 hour 37° C. 100 μL of the expression mix were plated on LB plates containing either 10 μg/mL kanamycin for the pGPS1 reaction or LB plates containing 12.5 μg/mL chloramphenicol for the pGPS2 reaction. 8 transformants from each reaction were analyzed. Plasmid DNA from all 16 colonies had a high molecular weight plasmid which ran on an agarose gel in approximately the same position as the plasmid DNA isolated from BRL3718. In addition, several of the plasmid DNAs were again electroporated into EMax DH10B cells and were shown to confer resistance to either kanamycin or chloramphenicol on the DH10B cells. It was concluded that the genes conferring resistance to either kanamycin or chloramphenicol had been introduced into the large molecular weight plasmid from BRL3718. DH10B cells containing the high molecular weight plasmid which confers resistance to kanamycin have been designated BRL3726. DH10B cells containing the high molecular weight plasmid which confers resistance to chloramphenicol have been designated BRL3727.

EXAMPLE 7

Construction of Deletion Plasmids.

Plasmid DNA from the strain BRL3726 (DH10B containing the high MW plasmid+$Km^r$ marker) was prepared. In two separate reactions, 1 μg of plasmid DNA was partially digested with 0.5 and 0.1 units of the restriction enzyme Sau3A I (Life Technologies, Inc.) at 37° C. for 15 min. The reactions were extracted with phenol/chloroform and precipitated with ethanol. The DNA from each reaction was ligated using $T_4$ DNA Ligase (Life Technologies, Inc) and transformed into competent ME DH5α cells (Life Technologies, Inc). Colonies were selected on LB plates containing 20 μg/mL kanamycin at 37° C. Chemically competent cells were used because they are not as efficient in taking up high molecular weight plasmid DNA as electrocompetent cells.

The plasmid DNA from 10 kanamycin resistant (from the 0.1 U reaction) colonies was analyzed by agarose gel electrophoresis. The size of the deletion plasmid DNA ranged from ~4.5–15 kb and the plasmids were designated deletion 1-deletion 10. DH5α cells containing these plasmids were designated BRL3740-1 to BRL3740-10.

EXAMPLE 8

Curing BRL3718 of the High Molecular Weight Plasmid DNA.

Chemically competent cells of BRL3718 were prepared according to the method of Hanahan (Hanahan D., 1983 J. Mol Biol 166,557) as modified according to U.S. Pat. No. 4,981,797. Chemically competent cells of BRL3718 were transformed with plasmid DNA isolated from BRL3740-1 (deletion 1, ~8 kb) and BRL3740-3 (deletion 3, ~10 kb) and kanamycin resistant colonies were selected on LB plates containing 20 μg/mL kanamycin at 37° C. Four colonies from each transformation were streaked for single-colony isolates onto LB plates containing 20 μg/mL kanamycin at 37° C. Plasmid DNA was isolated from 4, single-colony isolates and analyzed by agarose gel electrophoresis.

The high molecular weight plasmid DNA was readily apparent in miniprep DNA prepared from BRL3718. However, plasmid DNA prepared from the kanamycin resistant transformants did not indicate the presence of the high molecular weight plasmid DNA. Rather, plasmid DNAs with molecular weights characteristic of BRL3740-1 (~8 kb) and BRL3740-3 (~10 kb) were readily visible. It was concluded that the transformation of deletion 1 and deletion 3 plasmid DNA into BRL3718 resulted in replacement of the high molecular weight plasmid DNA (>50 kb) with deletion 1 and deletion 3 DNA. This is the expected result since the high molecular weight plasmid DNA, deletion 1 plasmid DNA and deletion 3 plasmid DNA all share the same origin of replication. The BRL3718 derivatives containing deletion 1 and deletion 3 plasmid DNA were designated BRL3741 and BRL3742, respectively.

EXAMPLE 9

Curing BRL3741 and 3742 of the $Km^r$ Plasmids.

BRL3741 and BRL3742 were grown overnight in LB broth containing 10% SDS at 30° C. The cultures were diluted 1:1000 into LB broth containing 10% SDS and incubated again at 30° C. After 2 cycles at 30° C., dilutions of these cultures (1:$10^4$ and 1:$10^6$) were applied to LB plates, incubated at 30° C., and screened for sensitivity to kanamycin. For BRL3741, 15/50 colonies were sensitive to kanamycin while 9/50 colonies from BRL3742 were sensitive to kanamycin. Plasmid DNA from 2 kanamycin sensitive derivatives of BRL3741 and 2 kanamycin sensitive derivatives of BRL3742 was isolated and analyzed by agarose gel electrophoresis. No plasmid DNA corresponding to the deletion plasmids was observed on the gel. The BRL3741 derivatives cured of the deletion 1 plasmid were designated BRL3756. The BRL3742 derivatives cured of the deletion 3 plasmid were designated BRL3757.

EXAMPLE 10

Competent Cells of BRL3756 and BRL3757.

Chemically competent cells of BRL3741, BRL3742, BRL3756 and BRL3757 were prepared according to the method of Hanahan (Hanahan D., 1983 J. Mol Biol 166,557) as modified according to U.S. Pat. No. 4,981,797. BRL3741 and BRL3742 were streaked on LB plates containing 20 μg/mL kanamycin and the plates were incubated at 28° C. for 20 hours. BRL3756(1), BRL3756(2), BRL3757(1) and BRL3757(2) were streaked on LB plates and the plates were incubated 28° C. for 20 hours. 5–6 colonies of each strain were picked into 1 mL SOB medium (D, Hanahan J. Mol Biol 166:557 1983). 0.9 mL of the cells were inoculated into 60 mL SOB medium in a 500 mL baffled shake flask. The flasks were placed in an 28° C. incubator 250 rpm. When the OD at 550 nm reached 0.25–0.33, the cells were harvested. 50 mL of cells of each strain were centrifuged (4° C.) and the cells were re-suspended in 4 mL cold CCMB80 buffer (D. Hanahan, J. Jessee and F. Bloom Methods in Enzymology 204:63 1991, specifically incorporated herein by reference). The cells were allowed to sit on ice for 20 min. 220 μL were placed in NUNC vials and the cells were frozen in a dry ice ethanol bath. The cells were stored at −70° C.

EXAMPLE 11

Evaluation of Time to Ampicillin Resistant Colony.

Vials of competent cells (ATCC9637, BRL3718, BRL3741, BRL3742, BRL3756 and BRL3757) were thawed on ice for 20 min. 100 μL of cells were mixed in a cold Falcon 2059 tube with pUC19 (5 μL of 10 pg/μL=50 pg). The cells were allowed to sit on ice for 15 min. The cells were heat shocked at 42° C. for 45 seconds followed by a 2 minute incubation on ice. 0.9 mL of room temperature SOC was added to each tube and the tubes were shaken at 37° C. (250 rpm) for 30 minutes. Aliquots of the expression mix were plated on LB plates containing 100 μg/mL ampicillin and the plates were incubated at either 42° C. or 37° C. The time to the appearance of 1 mm colonies is shown in table 2. At 37° C., ampicillin resistant colonies of 1 mm size required between 7.8 and 8.2 hours and there was no significant difference in time between strains containing both the 5.5 kb plasmid and the >50 kb plasmid (ATCC9637), strains containing only the >50 kb plasmid (BRL3718), strains containing the smaller kanamycin resistant plasmid (BRL3741 and 3742), or strains containing no plasmids (BRL3756 and 3757). In fact at 42° C. colonies of 1 mm size required 7.7 hours for all strains tested. It was concluded that the presence or absence of plasmids in *E. coli* W does not significantly affect the time to appearance of colonies after transformation.

EXAMPLE 12

Construction of BRL3734.

Electrocompetent cells of BRL3718 were prepared according to a modification of the protocol described in Hanahan et. al., Methods in Enzymology, vol. 204, p. 63 (1991). DNA from BRL3727 isolate $4_6$ was used to introduce the plasmid into BRL3718. 20 µL of cells were mixed with 1 µL of DNA and the cell-DNA mixture was electroporated at 250 V, 2000 ohms, 1.44 kV, 9.6 kV/cm in the Life Technologies Cell-Porator. 10 µL were expressed in 1 mL SOC for 60 min 37° C. and the expression was plated on LB plates containing 12.5 µg/mL chloramphenicol. After 24 hours the colonies were re-purified and analyzed. The miniprep DNA contained a plasmid with a molecular weight approximately the same size as the plasmid found in BRL3718. The *E. coli* W strain containing the chloramphenicol resistant high molecular weight plasmid was designated BRL3734.

EXAMPLE 13

Curing BRL3734 of the High Molecular Weight Plasmid DNA.

Chemically competent cells of BRL3734 were prepared according to the method of Hanahan (Hanahan D., 1983 J. Mol Biol 166,557) as modified according to U.S. Pat. No. 4,981,797. Chemically competent cells of BRL3734 were transformed with plasmid DNA isolated from BRL3740-1 (deletion 1, ~8 kb) and BRL3740-3 (deletion 3, ~10 kb) and kanamycin resistant colonies were selected on LB plates containing 20 µg/mL kanamycin at 37° C. Four colonies from each transformation were streaked for single-colony isolates onto LB plates containing 20 µg/mL kanamycin at 37° C. Plasmid DNA was isolated from 4, single-colony isolates and analyzed by agarose gel electrophoresis. The high molecular weight plasmid DNA was readily apparent in miniprep DNA prepared from BRL3734. However, plasmid DNA prepared from the kanamycin resistant transformants did not indicate the presence of the high molecular weight plasmid DNA. Rather, plasmid DNA with molecular weight characteristic of BRL3740-1 (~8 kb) and BRL3740-3 (~10 kb) were readily visible. Moreover, BRL3734 containing deletion 1 and deletion 3 plasmids were streaked for single-colony isolates onto LB containing Km 20 µg/mL and LB containing Cm 12.5 µg/mL plates to confirm the presence, or absence, of the desired plasmid DNAs. No growth was observed on the LB+Cm 12.5 µg/mL plates while the formation of single-colony isolates was observed on Km 20 µg/mL plates. It was concluded that the transformation of deletion 1 and deletion 3 plasmid DNA into BRL3734 resulted in replacement of the high molecular weight plasmid DNA (>50 kb) with deletion 1 and deletion 3 DNA. This is the expected result since the high molecular weight plasmid DNA, deletion 1 plasmid DNA and deletion 3 plasmid DNA all share the same origin of replication. The BRL3734 derivatives containing deletion 1 and deletion 3 plasmid DNA were designated BRL3745 and BRL3746, respectively.

EXAMPLE 14

Curing BRL3745 and 3746 of the Km$^r$ Plasmids.

BRL3745 and BRL3746 were grown overnight in LB broth containing 10% SDS at 30° C. The cultures were diluted 1:1000 into LB broth containing 10% SDS and incubated again at 30° C. After 2 cycles at 30° C., dilutions of these cultures (1:10$^6$) were applied to LB plates, incubated at 30° C., and screened for sensitivity to kanamycin. For BRL3745, 22/100 colonies were sensitive to kanamycin while 1/100 colonies from BRL3742 were sensitive to kanamycin. Plasmid DNA from 3 kanamycin sensitive derivatives of BRL3745 and the one kanamycin sensitive derivative of 3746 was isolated and analyzed by agarose gel electrophoresis.

No plasmid DNA corresponding to the deletion 1 and deletion 3 plasmids was observed on the gel after curing. The BRL3745 derivatives cured of the deletion 1 plasmid were designated BRL3762. The BRL3746 derivative cured of the deletion 3 plasmid were designated BRL3763.

EXAMPLE 15

Competent Cells of BRL3762 and BRL3763.

Chemically competent cells of BRL3745, BRL3746, BRL3762 and BRL3763 were prepared according to the method of Hanahan (Hanahan D., 1983 J. Mol Biol 166,557) as modified according to U.S. Pat. No. 4,981,797. BRL3745 and BRL3746 were streaked on LB plates containing 20 µg/mL kanamycin and the plates were incubated at 28° C. for 20 hours. BRL3762(1), BRL3762(2), and BRL3763(1) were streaked on LB plates and the plates were incubated 28° C. for 20 hours. 5–6 colonies of each strain were picked into 1 mL SOB medium(D, Hanahan J. Mol Biol 166:557 1983). 0.9 mL of the cells were inoculated into 60 mL SOB medium in a 500 mL baffled shake flask. The flasks were placed in an 28° C. incubator 250 rpm. When the OD550 nm reached 0.25–0.33 the cells were harvested. 50 mL of cells of each strain were centrifuged (4° C.) and the cells were re-suspended in 4 mL cold CCMB80 buffer (D. Hanahan, J. Jessee and F. Bloom Methods in Enzymology 204:63 1991). The cells were allowed to sit on ice for 20 min. 220 µL were placed in NUNC vials and the cells were frozen in a dry ice ethanol bath. The cells were stored at −70° C.

EXAMPLE 16

Evaluation of Time to Ampicillin Resistant Colony.

One vial of competent cells (ATCC9637, BRL3734, BRL3745, BRL3746, BRL3762 and BRL3763) was thawed on ice for 20 min. 100 µL of cells were mixed in a cold Falcon 2059 tube with pUC19 (5 µL of 10 pg/µL=50 pg). The cells were allowed to sit on ice for 15 min. The cells were heat shocked at 42° C. for 45 seconds followed by a 2 minute incubation on ice. 0.9 mL of room temperature SOC was added to each tube and the tubes were shaken at 37° C. (250 rpm) for 30 minutes. Aliquots of the expression mix were plated on LB plates containing 100 µg/mL ampicillin and the plates were incubated at either 42° C. or 37° C. The time to the appearance of 1 mm colonies is shown in table 3. At 37° C., ampicillin resistant colonies of 1 mm size required 8.0 hours and there was no significant difference in time between strains containing both the 5.5 kb plasmid and the >50 kb plasmid (ATCC9637), strains containing only the >50 kb plasmid (BRL3734), strains containing the smaller kanamycin resistant plasmid (BRL3745 and 3746), or strains containing no plasmids (BRL3762 and 3763). At 42° C., colonies of 1 mm size required 7.3 hours for all strains tested. It was concluded that the presence or absence of plasmids in *E. coli* W does not significantly affect the time to appearance of colonies after transformation. In addition, the data in tables 3 and 4 indicate that incubation of the LB ampicillin plates at 42° C. results in the appearance of ampicillin resistant colonies approximately 0.5 hours faster than on plates incubated at 37° C.

EXAMPLE 17

Comparison of Wildtype *E. coli* W and *E. coli* K-12.

Competent cells of *Escherichia coli* strains ATCC9637 (W), BRL3582 (*E. coli* W endA⁻ srl::Tn10 recA1398), and ATCC33625 (MM294) were prepared according to the method of Hanahan (Hanahan D., 1983 J. Mol Biol 166,557) as modified according to U.S. Pat. No. 4,981,797. The competent cells were prepared using CCMB80 buffer (Hanahan, D., Jessee, J., and Bloom, F. R., 1991, Methods in Enzymology 204,63). Max Efficiency DH5α competent cells were obtained from Life Technologies Inc.

The competent cells were thawed on ice for 20 minutes. 100 µL of the cells were transformed with 50 pg of pUC19 or 50 pg of pBR322 DNA. The cell-DNA mixture was placed on ice for 30 minutes and then heat shocked at 42° C. for 45 seconds. The tubes were then placed on ice for 2 minutes. 0.9 mL of SOC (Hanahan 1983) was added to each tube and the tubes were then shaken at 225 rpm for 1 hour at 37° C. Appropriate dilutions were spread on LB plates containing 100 µg/mL ampicillin and the plates were incubated at 37° C. The amount of time in hours to the appearance of 1 mm colonies was measured and is shown in Table 4. ATCC9637 yielded colonies in 8–8.5 hours compared to approximately 10 hours for ATCC33625, another recA⁺ strain. recA⁻ strains were also compared. BRL3582 yielded colonies in approximately 10 hours compared to 16 hours for DH5α.

EXAMPLE 18

Growth of Transformed Microorganisms at an Elevated Temperature.

Using the protocol described in the preceding example, the effects of growth an elevated temperature were analyzed. Incubating the transformed microorganisms on LB ampicillin plates at 42° C. resulted in the appearance of colonies from 0.5–1 hour faster compared to plates incubated at 37° C. Plating the cells on plates made from Circle Grow (Bio101) and containing ampicillin at 100 µg/mL resulted in the appearance of colonies from 0.5–1 hour faster compared to the appearance of colonies on LB plates containing ampicillin at 100 µg/mL. Thus, the use of elevated temperatures and/or enriched growth media may facilitate an increased growth rate of the microorganisms of the present invention.

EXAMPLE 19

Preparation of Derivatives of *E. coli* W Cured of Plasmids.

An isolate of *E. coli* W that has been cured of plasmid, such as BRL3762, BRL3763, BRL3756 or BRL3757, is used to construct derivatives having genotypes desirable for biotechnology applications. Using the P1 transduction technique described above, strains having one or more useful genetic alterations are prepared. Useful genetic alterations include: a recA⁻ genotype such as recA1/recA13 or recA deletions, a lacZ⁻ genotype that allows alpha complementation such as lacX74 lacZΔM15 or other lacZ deletion, a protease deficient genotype such as Δlon and/or ompT⁻, an endonuclease minus genotype such as endA1, a genotype suitable for M13 phage infection by including the F' episome, a restriction negative, modification positive genotype such as hsdR17($r_K^-$, $m_K^+$), a restriction negative, modification negative genotype such as hsdS20($r_B^-$, $m_B^-$), a methylase deficient genotype such as mcrA and/or mcrB and/or mrr, a genotype suitable for taking up large plasmids such as deoR, a genotype containing suppressor mutations such as supE and/or supF. Other suitable modifications are known to those skilled in the art and such modifications are considered to be within the scope of the present invention.

In a preferred embodiment, the rapid growing microorganisms of the present invention contains a modified lac operon that permits alpha complementation. In order to support alpha complementation, it was necessary to introduce a deletion into the N-terminal region of the genomic β-galactosidase gene. First, a lacX74 mutation was introduced into BRL3756 and BRL3757 by P1 transduction with a lysate prepared on BRL3759 which contains the lacX74 mutation linked to a Tn10 insertion. Strains containing the lacX74 insertion are tetracycline resistant as a result of the Tn10 insertion. Strains were selected on tetracycline containing plates and the resultant strains were designated BRL3760 (derived from BRL3756) and BRL3761 (derived from BRL3757). The strains were cured of the Tn10 insertion by growth in the presence of fusaric acid and the resultant tetracycline sensitive strains containing the lacX74 mutation were designated BRL3766 and BRL769. These strains were made competent using the modified method of Hanahan as disclosed above and were then transformed with plasmid containing the alpha fragment of the β-galactosidase gene. The plasmid containing strains were transduced using a lysate prepared on and *E. coli* strains carrying the ϕ80dlacZΔM15 deletion mutation linked to a Tn10 insertion in the tip gene. As a result of the insertion in the trp gene, strains carrying this mutation require tryptophan in the growth media. Tetracycline resistant strains were selected and were designated BRL3776 (derived from BRL3756 via BRL3760 and BRL3766) and BRL3778 (derived from BRL3757 via BRL3761 and BRL3769). These strains are lacX74 ϕ80dlacZΔM15 trp⁻::Tn10. To restore the wild type trp gene, strains BRL3776 and BRL3778 were transduced with a P1 lysate prepared on *E. coli* DH5α and selected on minimal media minus tryptophan. The strains were spontaneously cured of the alpha fragment containing plasmid and the final alpha complementation strains BRL3781 (from BRL3776) and BRL3784 (from (BRL3778) were isolated. These strains are lacX74 ϕ80dlacZΔM15. BRL3781 and BRL3784 were deposited at the Agricultural Research Service Culture Collection (NRRL, 1815 North University Street, Peoria, Ill., 61064) on Jun. 17, 1999. The deposits were made under the terms of the Budapest Treaty. BRL3781 has been given accession number NRRL No. B-30143 and BRL3784 has been given accession NRRL No. B-30144.

Those skilled in the art will appreciate that other modifications to the genome of the rapid growing microorganisms of the present invention are possible using the techniques described above. *E. coli* containing a desired mutation linked to a Tn10 insertion are readily available from sources well known to those skilled in the art. The desired mutation can be inserted into the genome of a rapid growing microorganism using P1 transduction and then the Tn10 can be cured by growth in the presence of fusaric acid.

In preferred embodiments, the rapid growing microorganisms of the present invention will carry an inducible T7 polymerase gene. In preferred embodiments, the T7 polymerase gene will be under the control of a salt inducible promoter as described by Bhandari, et al., J. Bacteriology, 179(13):4403–4406, 1997 which is specifically incorporated herein by reference. The T7 polymerase gene may be under the control of the salt inducible promoters of the proU locus. Alternatively, the T7 polymerase gene may be under the control of other salt inducible promoters. Other suitable inducible promoters include the lac promoter, the trp promoter, the tac promoter as well as any other inducible promoter known to those skilled in the art. The selection of the appropriate promoters and construction of strains carrying the T7 polymerase under the control of a given promoter are well within the abilities of those of ordinary skill in the art. Optionally, embodiments containing an inducible T7 polymerase gene may contain mutations in one or more protease genes and mutations in one or more ribonuclease genes. Such mutations may be inserted into the genome using the methods described above.

EXAMPLE 20

Identification of Rapid Growing Microorganisms

Other microorganisms will be screened to identify rapid growing strains. Isolates to be screened are plated on an appropriate solid medium and grown to a defined colony size. The time to reach the defined colony size is compared to the time taken by an E. coli K or other strains described herein to reach the same colony size. The microorganisms to be screened include, but are not limited to, microorganisms such as those of the genera Escherichia sp. (particularly E. coli and, more specifically, E. coli strains B, C, W and K)), Klebsiella sp., Streptomyces sp., Streptococcus sp., Shigella sp., Staphylococuss sp., Erwinia sp., Klebsiella sp., Bacillus sp. (particularly B. cereus, B. subtilis, and B. megaterium), Serratia sp., Pseudomonas sp. (particularly P. aeruginosa and P. syringae) and Salmonella sp. (particularly S. typhi or S. typhimurium). A plasmid conferring an antibiotic resistance is transformed into the microorganism to screened using the techniques described above. The transformed microorganisms are then plated on a solid medium containing antibiotic and then incubated at an appropriate temperature until colonies of a defined size are observed.

EXAMPLE 21

Cloning Using Rapid Growing Microorganisms.

The rapid growing microorganisms identified above may be used to clone DNA fragments. A population of recombinant vectors comprising a DNA insert having a desired sequence is constructed as described above. The vector may contain a DNA sequence coding for an antibiotic resistance gene and/or may contain one or more marker genes. The population of recombinant vectors is transformed into a rapid growing microorganism rendered competent by any conventional technique. For example, the microorganism is rendered competent by chemical means using the technique of Hanahan discussed above. Alternatively, the microorganism is made competent for electroporation by removing the growth media and placing the microorganism in a medium of low ionic strength. Any method of making the microorganism competent that allows the microorganism to take up exogenously applied DNA and, in particular, recombinant plasmids, is suitable for the practice of the instant invention.

Competent microorganisms are contacted with some or all of the population of recombinant vectors under conditions suitable to cause the uptake of the recombinant vectors into the competent microorganism. Suitable conditions may include a heat shock. For example, the mixture of cells and population of recombinant vectors are heated to 42° C. for 45 seconds. Alternatively, suitable conditions may include subjecting a mixture of microorganism and recombinant vector to an electric field.

After the recombinant vector is taken up by the microorganism, the microorganism is grown for a period of time sufficient to allow the expression of an antibiotic resistance gene. After any such period, the microorganism containing the recombinant vector is spread on plates containing the appropriate antibiotic and incubated until colonies are visible. In a preferred embodiment, the plates are incubated from about 4 hours to about 16 hours. In other preferred embodiments, the plates are incubated from about 4 hours to about 8 hours and in other preferred embodiments, the plates are incubated from about 4 hours to about six hours. In a preferred embodiment, the incubation step is performed at a temperature above 37° C. at which temperature the microorganism containing the recombinant plasmid grows more rapidly than it grows at 37° C. In another preferred embodiment, the incubation step is performed at 42° C.

After colonies become visible, some or all of the colonies will be selected to be grown in liquid culture. The selection process may be by any conventional means. In a preferred embodiment, the microorganism and vector will permit alpha complementation and the selection is by blue/white screening on X-gal plates in the presence of IPTG. In other preferred embodiments, the selection is by detecting the presence or absence of a marker gene present on the vector. Suitable marker genes include, but are not limited to, the gene coding for luciferase, the gene coding for chloramphenicol acetyl transferase and the gene coding for β-glucuronidase.

The selected colonies are grown in liquid culture for a period of time sufficient to produce a quantity of recombinant microorganisms suitable for analysis. The recombinant vector will be isolated from the microorganisms. In a preferred embodiment, the period of growth in liquid culture will be from about 2 hours to about 16 hours. In other preferred embodiments, the period of growth in liquid culture will be from about 2 hours to about 8 hours and in other preferred embodiments, the period of growth in liquid culture will be from about 2 hours to about 4 hours.

The recombinant vector is isolated by any conventional means. In a preferred embodiment, the recombinant vector is isolated by an alkaline lysis "mini-prep" technique. Optionally, the isolation may employ a column purification step. The isolated vector is analyzed by any conventional technique, for example, by agarose gel electrophoresis of the plasmid with or without prior digestion of the plasmid with one or more restriction enzymes. Other suitable techniques include sequencing of the plasmid. Techniques for determining the DNA sequence of a plasmid are well known to those skilled in the art.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

TABLE 1

List of strains used in the experiments

| Strain | Relevant Genetic Markers | Plasmids 5.5 kb | 6.5 kb | >50 kb | other |
|---|---|---|---|---|---|
| *E. coli* W | | | | | |
| ATCC9637 | | + | | + | |
| BRL3234 | P1 sensitive of ATCC9637 | | | | |
| BRL3234/pCM301 | amp resistant temp sensitive | | | | pCM301 |
| BRL3573 | nupG::Tn10 endA$^-$ | | | | pCM301 |
| BRL3574 | nupG::Tn10 endA$^-$ | | | | |
| BRL3580 | endA$^-$ | + | | + | |
| BRL3582 | As 3580 endA srl::Tn10 recA deletion 1398 | | | | |
| BRL3711 | endA- | | + (Apr) | + | |
| BRL3718 | endA$^-$ | − | | + | |
| BRL373410 | endA$^-$ | | | + (Cm$^r$) | |
| BRL3741 | As 3718 | − | | − | deletion 1 (Km$^r$) |
| BRL3742 | As 3718 | − | | − | deletion 3 (Km$^r$) |
| BRL3756 | SDS curing of 3741 | − | | − | |
| BRL3757 | SDS curing of 3742 | − | | − | |
| BRL3745 | As 3734 | − | | − | deletion 1 (Km$^r$) |
| BRL3746 | As 3734 | − | | − | deletion 3 (Km$^r$) |
| BRL3762 | SDS curing of 3745 | − | | − | |
| BRL3763 | SDS curing if 3746 | − | | − | |
| BRL3759 | DH10B recA$^+$ zah281::Tn10 lacX74 | | | | |
| BRL3764 | DH10B recA$^+$ trp::Tn10 φ80dlacZΔM15 | | | | |
| BRL3760 | lacX74 zah281::Tn10 | | | | |
| BRL3761 | lacX74 zah281::Tn10 | | | | |
| BRL3766 | lacX74 | | | | |
| BRL3766/pSU39 | lacX74 | | | | pSU39 |
| BRL3769 | lacX74 | | | | |
| BRL3769/pSU39 | lacX74 | | | | pSU39 |
| BRL3776 | lac74 trp-::Tn10 φ80dlacZΔM15 | | | | pSU39 |
| BRL3778 | lac74 trp-::Tn10 φ80dlacZΔM15 | | | | pSU39 |
| BRL3781 | lac74 trp-::Tn10 φ80dlacZΔM15 | | | | |
| BRL3776 | lac74 trp-::Tn10 φ80dlacZΔM15 | | | | |
| *E. coli* K-12 | | | | | |
| DB3.2 | nupG::Tn10 endA$^-$ | | | | |
| DH10B | endA$^-$ | | | | |
| BRL3709 | As DH10B | + (Ap$^r$) | | | |
| BRL3726 | As DH10B | | | + (Km$^r$) | |
| BRL3727 | As DH10B | | | + (Cm$^r$) | |
| DH5α | | | | | |
| BRL3740(1) | As DH5α | | | | deletion 1 (Km$^r$) |
| BRL3740(3) | As DH5α | | | | deletion 3 (Km$^r$) |
| *E. coli* C | | | | | |
| BRL3229 | *E. coli* C srl$^-$::Tn10 recA deletion 1398 P1Cm$^{ts}$ | | | | |

TABLE 2

Time in hours to ampicillin resistant colonies after transformation with pUC19 DNA.
Time to 1 mm colony size

| STRAIN | 42° C. | 37° C. |
|---|---|---|
| ATCC 9637 | 7.7 | 8.2 |
| BRL3718 | 7.7 | 7.8 |
| BRL3741 | 7.7 | 8.2 |
| BRL3742 | 7.7 | 7.8 |
| BRL3756 (1) | 7.7 | 8.2 |
| BRL3756 (2) | 7.7 | 8.2 |
| BRL3757 (1) | 7.7 | 7.8 |
| BRL3757 (2) | 7.7 | 8.2 |

TABLE 3

Time in hours to ampicillin resistant colonies after transformation with pUC19 DNA.
Time to 1 mm colony size

| STRAIN | 42° C. | 37° C. |
|---|---|---|
| ATCC 9637 | 7.3 | 8.0 |
| BRL3734 | 7.3 | 8.0 |
| BRL3745 | 7.3 | 8.0 |
| BRL3746 | 7.3 | 8.0 |
| BRL3762 (1) | 7.3 | 8.0 |
| BRL3762 (2) | 7.3 | 8.0 |
| BRL3763 | 7.3 | 8.0 |

TABLE 4

| | Time in hours to ampicillin resistant colonies after transformation with pUC19 DNA Time to 1 mm colony size | |
|---|---|---|
| STRAIN | pUC19 | pBR322 |
| ATCC 9637 (W) recA⁺ | 8.0 | 8.5 |
| BRL3582(6) W recA⁻ | 10.25 | ND |
| MM294 recA⁺ | 10.25 | 10.25 |
| DH5α recA⁻ | 16.0 | 16.0 |

What is claimed is:

1. An isolated, competent *E. coli* that exhibits visible colonies 7.8 to 8.5 hours after transformation and incubation on LB agar at 37° C., wherein said *E. coli* is suitable for alpha-complementation and selection by blue/white screening.

2. The competent *E. coli* according to claim 1, wherein said colonies are 1 mm in size.

3. The competent *E. coli* according to claim 1, wherein said *E. coli* is a K12 derivative.

4. The competent *E. coli* according to claim 1, wherein said *E. coli* is lacZ⁻.

5. The competent *E. coli* according to claim 4, wherein said *E. coli* is lacZ⁻.

6. The competent *E. coli* according to claim 1, wherein said *E. coli* is recA⁻.

7. The competent *E. coli* according to claim 1, wherein said *E. coli* is restriction negative.

8. The competent *E. coli* according to claim 1, wherein said *E. coli* is modification negative.

9. The competent *E. coli* according to claim 1, wherein said *E. coli* is restriction negative and modification negative.

10. The competent *E. coli* according to claim 1, wherein said *E. coli* is methylase deficient.

11. The competent *E. coli* according to claim 10, wherein said *E. coli* is mcrA⁻.

12. The competent *E. coli* according to claim 10, wherein said *E. coli* is mcrB⁻.

13. The competent *E. coli* according to claim 1, wherein said *E. coli* is endonuclease deficient.

14. The competent *E. coli* according to claim 13, wherein said *E. coli* is endA1.

15. The competent *E. coli* according to claim 3, wherein said *E. coli* is lacZ⁻, restriction negative, methylase deficient, and endonuclease deficient.

16. The competent *E. coli* according to claim 15, wherein said *E. coli* is lacZ⁻, mcrB⁻, and endA1.

* * * * *